United States Patent [19]

Aoyagi

[11] Patent Number: 5,061,450
[45] Date of Patent: Oct. 29, 1991

[54] ISOLATION FLUID CONTROL DEVICE AND WATER CUP

[75] Inventor: Keichi Aoyagi, Westfield, N.J.

[73] Assignee: Technicon Instruments Corporation, Tarrytown, N.Y.

[21] Appl. No.: 58,702

[22] Filed: Jun. 5, 1987

Related U.S. Application Data

[63] Continuation of Ser. No. 736,602, May 21, 1985, abandoned.

[51] Int. Cl.⁵ .............................................. B01L 11/00
[52] U.S. Cl. ..................................... 422/101; 422/102; 422/106; 436/177; 436/178; 73/290 R; 137/101.25; 137/101.27; 210/299; 210/644
[58] Field of Search ......................... 422/101, 102, 106; 436/177, 178; 73/290 R; 137/101.25, 101.27; 210/299, 644

[56] References Cited

U.S. PATENT DOCUMENTS 3,539,300  11/1970  Stone ........................ 436/177 X
3,656,912  4/1972   Sugawara ..................... 422/101
4,025,679  5/1977   Denny ......................... 210/508 X
4,388,407  6/1983   Lepain et al. ................. 436/177 X

FOREIGN PATENT DOCUMENTS 0048593  9/1910  Fed. Rep. of Germany ...... 422/101

OTHER PUBLICATIONS

Bush and Goth, "Laboratory Spray Extraction Column", Ind. & Engin. Chemistry (Anal. Ed.), vol. 16, Aug. 1944.

Primary Examiner—Lynn Kummert
Attorney, Agent, or Firm—Jeffrey M. Greenman

[57] ABSTRACT

An isolation fluid control device and water cup for use in an automated, random-access, isolation fluid-based, analytical instrument. The cup, in operation, contains two immiscible liquids. The cup is provided with inlets and outlets, and additionally comprises a liquid level control structure and structure operable to permit passage of one liquid therethrough to the substantial exclusion of the other liquid.

4 Claims, 3 Drawing Sheets

ISOLATION FLUID CONTROL DEVICE AND WATER CUP

This is a continuation of co-pending application Ser. No. 736,602, filed on May 21, 1985, now abandoned.

BACKGROUND OF THE INVENTION

1. Field of the Invention

The present invention relates to a device for use in a random access, isolation fluid-based, analytical instrument. More particularly, the invention is directed to a wash cup for use with such instrument whereby fresh water, test sample, and isolation fluid, all of which being necessary for the operation of the instrument, can be introduced therein.

Prior art devices which are presently in use with systems such as that described above suffer from an inherent disadvantage. The isolation fluid normally used in such devices is a fluorinated oil having a specific gravity significantly greater than water. Accordingly, segments of the fluid settle to the bottom of the sampling device or wash cup, and disrupt the water level regulating activity of the cup. The present invention completely overcomes this serious difficulty representative of the prior art.

2. Present State of the Art

The present invention relates to, and is directly usable in conjunction with, a random access, isolation fluid-based analytical instrument. In such systems, conduits are used, the inner walls of which are coated with immiscible liquid, such as a fluorinated oil. In use, the reagent to be utilized in a particular assay and/or the test sample to be assayed proceeds past one or more detection stations which, for example, can comprise a spectrophotometer or colorimeter, and discrete quantities of the test sample and/or reagents may be separated by air or other separating fluid. In order to avoid such inadvertent mixing of the discrete liquid samples, the walls of the conduit are coated with an immiscible liquid such as is described in the Smythe, et al., U.S. Pat. No. 3,479,141, assigned to the instant assignee. The Smythe, et al patent discloses a transport system for an automatic analysis apparatus in which a series of aqueous liquid samples are processed as a flowing fluid stream with substantially no contamination between the flowing liquid segments. A fluoropolymer conduit, such as TEFLON ® polymer, and intersample carrier segments of silicone are employed. Smythe, et al. teach that the silicone encapsulates aqueous liquid segments, substantially completely eliminating the intermixing of successive liquid segments. Reagents are separately introduced on a continual basis, such as in conventional fashion as described with respect to previous continuous-flow systems.

In Smythe, et al., U.S. Pat. No. 4,253,846, also assigned to the instant assignee, selective injection of reagent into a moving stream of sample segments is provided to such a continuous flow system, and allows for an increase in the efficiency and throughput of sample processing. Using injectors such as poppet valves, the reagent is introduced by piercing the immiscible liquid layer encapsulating the selected sample segments. The immiscible liquid layer reforms after injection to maintain sample integrity and prevent carryover to other samples in the system. Air and sample are alternately aspirated via a probe which periodically dips into a sample cup. The immiscible liquid is said to be introduced to the inlet end of the probe by an applicator (not shown) and aspirated along with air between successive sample immersions. The immiscible liquid can be a fluorocarbon and both the conduit wall and the poppet valve tip can be a fluorinated polymer. This patent does not further address the actual mechanism of immiscible liquid introduction and clearly indicates that it is separate from the "on-line" introduction of reagent.

Diebler, et al., U.S. Pat. No. 4,121,466, also assigned to the instant assignee, disclose a metering apparatus useful to either dispense or aspirate sample. The surface of the aspirating probe is coated with an immiscible liquid film which, in the preferred embodiment, is flowed continuously down the peripheral probe surface at a rate substantially equal to the aspiration rate, so as to be eventually aspirated into the probe inlet. During immersion, excess immiscible liquid on the peripheral probe surface floats onto the surface of the liquid being aspirated but a small film remains on the probe surface. Also, during aspiration, a thin film of immiscible liquid continuously wets the interior probe surface. As the probe is withdrawn, the flow of immiscible liquid is commenced so as to be aspirated along the probe immediately upon withdrawal thereof from the liquid. Segments of the immiscible liquid and aspirated liquid are therefore successively passed along the probe system.

Smythe, et al., U.S. Pat. No. 4,259,291, also assigned to the instant assignee, refers to the continuous flow systems described in the above Smythe, et al '291 and Diebler, et al '466 patents and addresses the need for more precise and uniform application of protective immiscible liquid coatings. An applicator directly surrounds the probe and layers a thin uniform film of immiscible liquid on the outer surface thereof. The applicator is moved relative to the probe to coat its outer surface. An aspirating mechanism connected to the probe alternately aspirates controlled volumes of air and aqueous sample therethrough. Immiscible liquid is said to be drawn into the probe along with the air segments so aspirated. Thus, alternating sample and air segments encased within the immiscible liquid are passed along the probe to a rotary valve which transfers each aspirated aqueous sample in turn from the probe to a conduit for dispensing to an analytical system. As described herein, a pool of wiped immiscible liquid forms about the probe due to the interplay of surface forces of the liquid in combination with the wetting forces of the immiscible liquid with respect to the probe surface. When the probe is withdrawn from the sample cup, this pool forms a small globule of immiscible liquid over the inlet of the probe, inasmuch as it preferentially wets the probe material to the substantial exclusion of the aqueous sample. This patent teaches that the globule of immiscible liquid is aspirated into the probe inlet along with an air segment. Reagent is introduced "downstream" in a manner which is not further described.

Each of the above patents has provided an advance of one sort or another in the elimination of successive sample intermixing and carryover. This end has been widely recognized as a major consideration in the improvement of continuous flow systems. The combined references provide a significant background literature on the technology available to prevent interaction of segments in continuous flow analysis systems, and the disclosure of the references are hereby incorporated herein by reference thereto.

Other aspects of the state of the art which are pertinent to the present invention include two continuous flow assay instruments currently marketed by the assignee herein, Technicon Instruments Corporation, namely the Simultaneous Multichannel Analyzer"(SMA ®) and the Simultaneous Multichanneled Analyzer with Computer (SMAC ®). Both of these instruments utilize a mechanized probe for transferring a test sample and the reagent liquids into the flowing stream. However, in order to minimize cross-contamination between successive samples, it is necessary to wash the probe. Accordingly, a washing cup is utilized with these instruments. Thus, the washing cup serves (a) to remove remnants of prior samples taken by the probe, i.e., (b) to clean the probe, (c) to inject successive aqueous samples into the flowing stream, (d) to assure a continuous flow of fresh water through the cup, and (e) to assure that the liquid level remains relatively constant, thereby providing a relatively constant volume of fresh water for the instrument.

SUMMARY OF THE INVENTION

Briefly stated, the present invention comprises a cup for use with a random access, isolation fluid based analytical instrument, and serves to contain a first liquid and a second liquid which are substantially immiscible with one another. The cup is provided with an inlet means and an outlet means, the former of which permits inlet to the cup of the second liquid, the latter of which permits outlet from the cup of the second liquid and a portion of the first liquid. The cup also comprises a liquid level control means for maintaining the level of liquid in the cups at a predetermined height or level, and which communicate with the cup and the outlet means. Additionally, the cup comprises a means operable to permit passage of the first liquid through it, but which selectively substantially excludes the passage of the second liquid therethrough.

OBJECTS OF THE INVENTION

Accordingly, it is an object of the present invention to provide a cup for use with a random access isolation fluid-based analytical instrument which enables automatic adjustment of the level of the liquid in the cup while simultaneously precluding buildup in or excessive accumulation of, an isolation fluid.

Another object of the invention is to provide a cup as above in which any isolation fluid which accumulates in the cup during its use is easily removable through the bottom of the cup.

Another object of the invention is to provide a cup as described above which is relatively simple and inexpensive to fabricate, and which is of one-piece construction having no moving parts.

Another object of the invention is to provide a cup as described above which is particularly adapted for use in an automated sample liquid analysis system utilizing an isolation fluid for introducing the isolation fluid into the analysis system.

Another object of the invention is to facilitate the introduction of aqueous, test samples into the analysis system.

A further object of the invention is to provide a cup as described above which is particularly adapted for use in conjunction with an instrument capable of analyzing body fluids such as blood, serum, urine and spinal fluids.

DESCRIPTION OF THE DRAWINGS

The foregoing objects of the invention, and others, as well as the significant advances in the art represented by the present invention, are set forth in detail in the following description of the invention. The accompanying drawings are provided to further clarify various aspects of the present invention.

Accordingly, FIG. I depicts a prior art device used on the SMA analytical system, and is a cross-sectional view of the said device.

Figure 1:
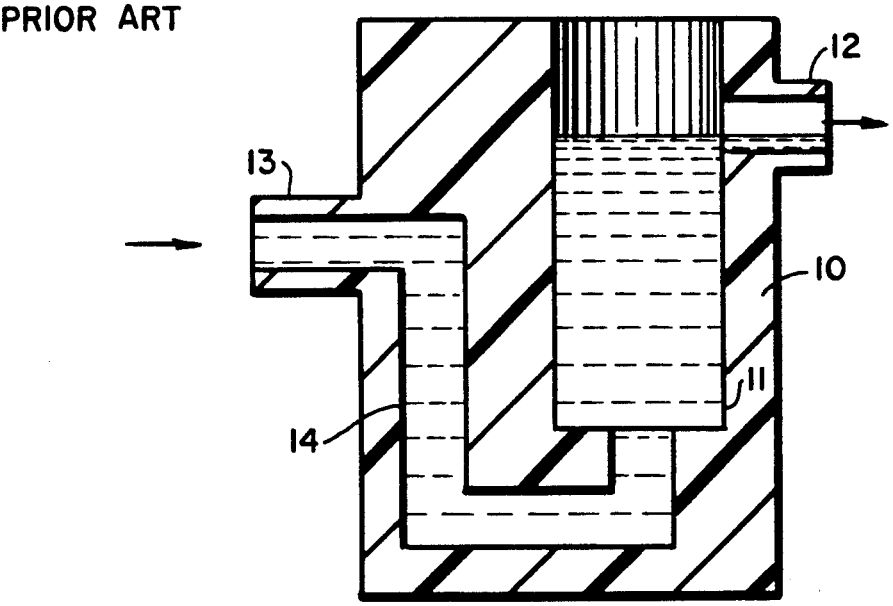
Figure 2:
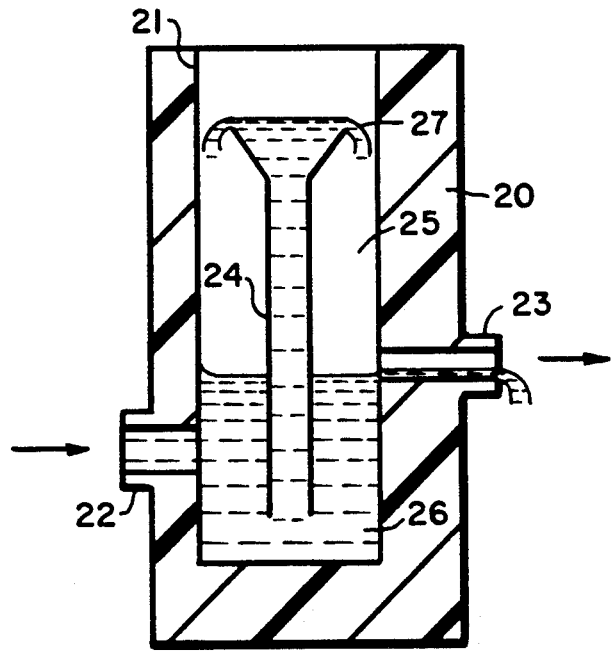
Figure 3:
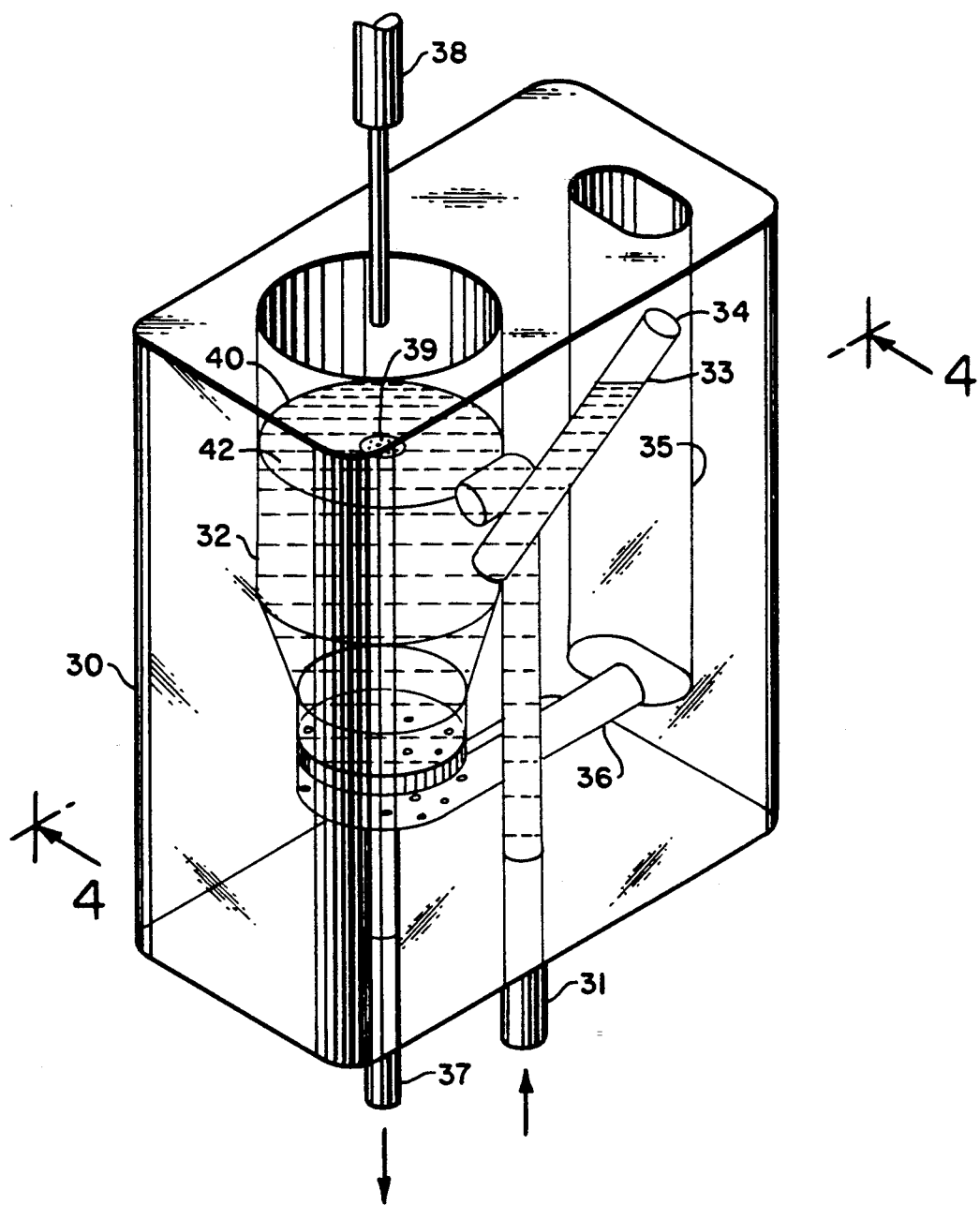
Figure 4:
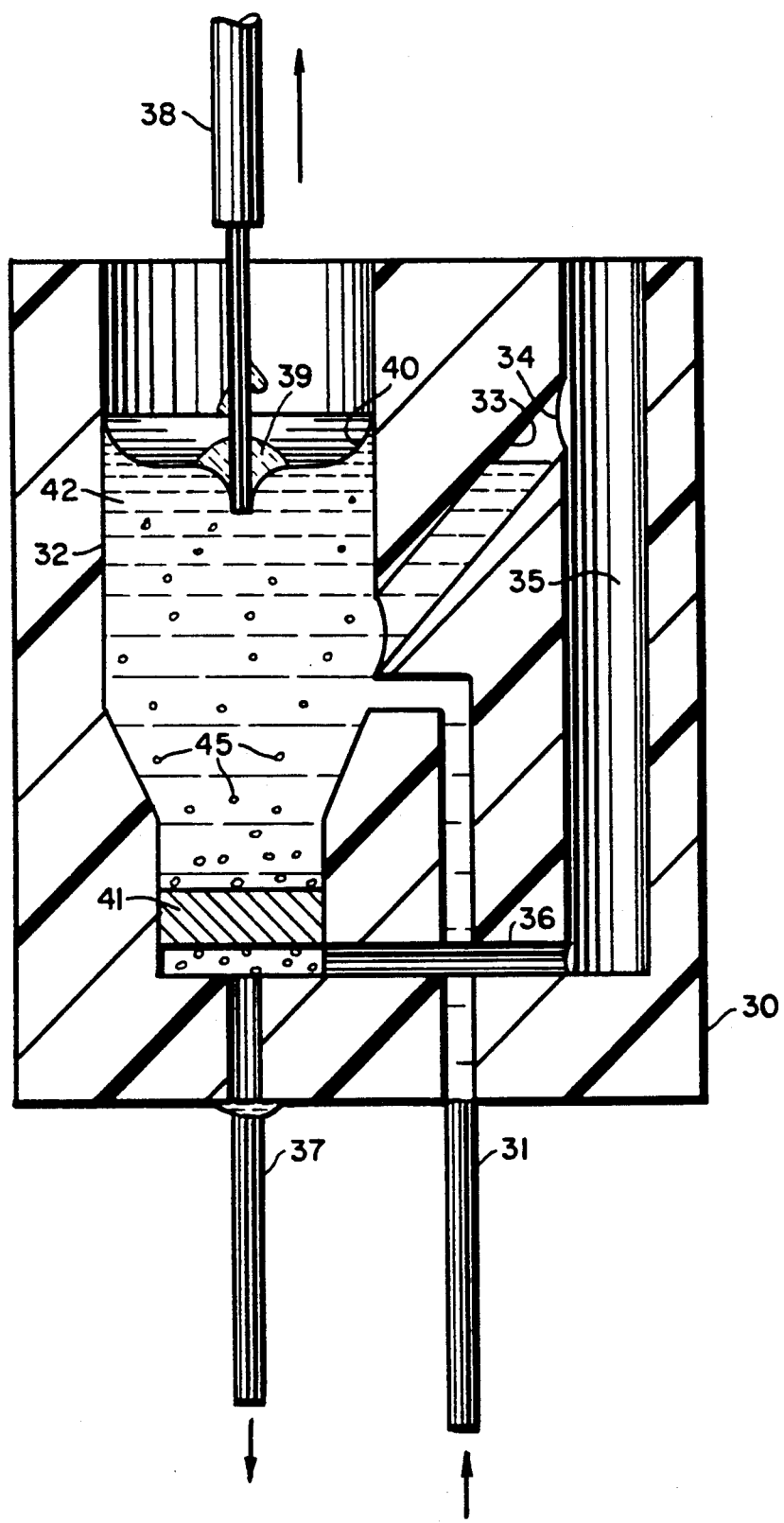

Similarly, FIG. II is a cross-sectional representation of a washing cup used with the SMAC analytical system mentioned above, and is a cross-sectional view thereof.

FIG. III is an isometric view of the present invention.

FIG. IV is a cross-sectional view of the present invention along lines 4—4 in FIG. III.

DETAILED DESCRIPTION OF THE PRESENT INVENTION

Referring initially to FIGS. I and II, washing cups are depicted for cleaning the sample injection probe of the SMA and SMAC systems, respectively, both of which are commercially available from the assignee herein, i.e., Technicon Instruments Corporation.

In FIG. I, the washing cup 10 comprises a generally two body member 11 having an outlet 12 and an inlet 13. Inlet 13 communicates with the body member 11 through conduit 14.

In operation in conjunction with the SMA analytical system, water enters inlet 13 and is permitted to flow through conduit 14, thereby filling body member 11 until it reaches a level at or near the bottom of outlet 12. Accordingly, water flows entirely through the washing cup thereby maintaining a relatively clean flow of water.

No provision is made, however, for use of such a cup with a random access, isolation fluid-based analytical instrument such as is described in the Smythe, et al. patents, mentioned supra.

Referring to FIG. II, there is depicted a washing cup 20 which is used with the commercially available SMAC analytical system, marketed by the present assignee, Technicon Instruments Corporation. Accordingly, washing cup 20 comprises a generally tubular body member 21 provided with inlet means 22 and an outlet means 23. Mounted within the body member 21 is an overflow means 24, which is mounted in such a way as to provide upper chamber 25 and lower chamber 26. Water which enters through inlet means 22 into lower chamber 26 travels up the overflow means 24 until it reaches lip 27, whereupon the water overflows into upper chamber 25 and leaves the apparatus through outlet means 23.

Turning now to the present invention, a preferred embodiment is depicted in FIGS. III and IV which illustrate the preferred elements of the invention. Accordingly, FIG. III depicts an isometric view of a preferred cup in accordance with the present invention, and FIG. IV is a cross-section of the cup along the lines 4—4 of FIG. III.

In FIGS. III and IV, the body of the cup 30 is comprised of any suitable material such as a clear plastic similar to acrylic. The cup is formed through any suitable means such as molding, extrusion, machining, or combinations of such processes or other processes, all of which are known to those skilled in the art.

Accordingly, inlet means 31 communicates with the cup portion 32, and the second liquid 42 enters the cup therethrough. As the level of the second liquid rises in cup 32, it simultaneously rises in overflow communication means 33. Communication means 33, together with overflow chamber 35 comprise the liquid level control means in the preferred embodiment. As liquid enters the cup and rises to level 34, it overflows into the overflow chamber and exits through conduit 36 and outlet means 37.

The first liquid, which is immiscible with the second liquid is introduced into the cup via probe 38 which has been coated on its perimeter with the first liquid prior to its insertion into the cup 30. Upon immersion into the second liquid present in the cup, a small portion of the first liquid remains behind upon removal of the probe 38. Because of its immiscibility with the second liquid, the first liquid forms lens 39, and floats at the surface 40 of the second liquid present in the cup due to surface tension.

Where the first liquid is of substantially higher specific gravity than the second liquid, as the lens forms, it eventually reaches a critical mass whereupon the weight of the lens partially overcomes the surface tension of the second liquid 42. This permits small portions 43 of the first liquid to settle to the bottom of the cup leaving the lens in position at the surface of the second liquid.

In order to prevent the first liquid from accumulating to any appreciable extent in the cup, a means 41 is provided to permit the passage of the first liquid out of the cup eventually to leave the cup through outlet means 37. Ideally, the means 41 is porous poly(tetrafluoroethylene) known commercially as Teflon trademark of E. I. DuPont de Nemours of Wilmington, Delaware. Of course, it is understood that means 41 can be comprised of any suitable material which will permit the passage of the first liquid from cup 32 to outlet means 37 to the substantial exclusion of the second liquid such as a porous halogenated hydrocarbon polymer. In the preferred embodiment, means 41 is a porous Teflon plug having a pore size of from about 5 to 15 microns. Especially preferred is a Teflon plug having a pore size in the range of about 5 to 15 microns.

What is claimed is:

1. A cup for the containment and separation of two immiscible liquids comprising:
   (a) a liquid receiving chamber constructed and arranged to receive a non-aqueous first liquid;
   (b) means for introducing an aqueous second liquid into said liquid receiving chamber, the second liquid being substantially immiscible with the first liquid and having a lower specific gravity than the first liquid, the first liquid forming a lens at the surface of the second liquid;
   (c) outlet means constructed and arranged to permit liquid to pass from said liquid receiving chamber;
   (d) liquid level control means constructed and arranged to maintain the level of the lens in said chamber at a preselected height, said liquid level control means including conduit means in fluid communication with said liquid receiving chamber configured so as to cause the second liquid within said liquid receiving chamber to overflow into an overflow chamber when the level of the second liquid rises above a predetermined point and whereby the level of the lens in said chamber is determined by the height of said conduit means; and
   (e) means for separating the first liquid from the second liquid in said liquid receiving chamber which means includes a porous fluid—selective filter means positioned at the bottom of said fluid receiving chamber between said fluid receiving chamber and said outlet means, said filter means permitting the passage therethrough of the non-aqueous first liquid settling from the lens to the substantial exclusion of the aqueous second liquid.

2. The cup of claim 1 in which said filter means comprises a porous halogenated hydrocarbon polymer.

3. The cup of claim 2 in which said filter means comprises porous poly(tetrafluoroethylene).

4. The cup of claim 2 in which the pore size of said filter means is from about 5 to 15 microns.

* * * * *